(12) United States Patent
Nissilä et al.

(10) Patent No.: US 6,520,920 B2
(45) Date of Patent: Feb. 18, 2003

(54) ARRANGEMENT FOR MEASURING BIOSIGNAL

(75) Inventors: Seppo Nissilä, Oulu (FI); Jari Miettinen, Oulu (FI)

(73) Assignee: Polar Electro Oy, Kempele (FI)

( * ) Notice: Subject to any disclaimer, the term of this patent is extended or adjusted under 35 U.S.C. 154(b) by 0 days.

(21) Appl. No.: 09/783,788

(22) Filed: Feb. 15, 2001

(65) Prior Publication Data

US 2001/0020134 A1 Sep. 6, 2001

(30) Foreign Application Priority Data

Feb. 16, 2000 (FI) .............................. 20000346

(51) Int. Cl.[7] .............................. A61B 5/02; A61B 5/00
(52) U.S. Cl. ................. 600/503; 600/485; 600/500; 600/300
(58) Field of Search ................. 600/503, 300, 600/481, 485, 490, 500, 501, 502

(56) References Cited

U.S. PATENT DOCUMENTS 4,307,727 A   12/1981  Haynes
5,240,007 A * 8/1993  Pytel et al. ............. 600/485
5,243,992 A   9/1993  Eckerle et al.
5,590,649 A   1/1997  Caro et al.
5,622,180 A   4/1997  Tammi et al.
5,640,964 A * 6/1997  Archibald et al. ........ 600/490
5,738,800 A * 4/1998  Hosali et al. ............ 216/89
5,908,027 A * 6/1999  Butterfield et al. ....... 600/485
6,290,650 B1 * 9/2001  Butterfield et al. ....... 600/485

FOREIGN PATENT DOCUMENTS

EP      0333442 A1   9/1989
JP      10146322     6/1998

* cited by examiner

*Primary Examiner*—Kevin Shaver
*Assistant Examiner*—Navin Natnithithadha
(74) *Attorney, Agent, or Firm*—Hoffmann & Baron, LLP

(57) ABSTRACT

The invention relates to an arrangement for measuring a biosignal from the surface of the skin of a living human body. The arrangement comprises a casing (5) on which a measuring sensor (300) rests which is to be arranged against a measurement target (1) on the body, and a fastener (6) for fastening the casing (5) to the measurement target (1). The arrangement is characterized by comprising an element (7), such as a spring element, which rests on the casing (5) and the fastener (6) such that the element (7) is arranged to turn the casing (5) substantially towards the measurement target (1) with respect to the fastener (6).

40 Claims, 6 Drawing Sheets

ARRANGEMENT FOR MEASURING BIOSIGNAL

BACKGROUND OF THE INVENTION

1. Field of the Invention

The invention relates to an arrangement for measuring a biosignal from a living body.

The invention is applied particularly to wristband-type devices for measuring a biosignal non-invasively, such as heart rate monitors, which measure a pressure pulse signal produced by the wrist artery pulse and determine the pulse frequency of the heart on the basis of this signal. Another preferred field of application is measurement of the pressure pulse measured in connection with blood pressure measurement. The invention may also be applied to a multipurpose measuring arrangement wherein pulse, blood pressure and other variables that can be obtained on the basis of the pressure signal are measured.

2. Brief Description of the Related Art

The prior art measuring arrangements are characterized in that a casing comprising a measuring sensor which produces measurement data is tightened around the wrist at the wrist artery by means of the pressing force caused by a fastener of the device.

Nevertheless, such a solution is seriously problematic since the entire casing is pressed by an equal force against the surface of the skin over the entire area covered by the fastener. Such a solution is sensitive to changes in the position of the wrist. When a wrist whereto a heart rate monitor has been attached for measuring the pulse e.g. during an exercise is moved during the exercise, the contact of the measuring arrangement with the surface of the skin and the wrist artery underneath the surface of the skin varies according to the position of the wrist. This impairs the measuring accuracy and sensitivity of the measuring arrangement. The contact of the sensor with the surface of the skin as well as the measuring accuracy of the sensor thus vary according to the position of the wrist, which makes the measurement less reliable.

SUMMARY OF THE INVENTION

An object of the present invention is to provide an improved arrangement for measuring a biosignal, an object of the arrangement being to improve the contact of the measuring sensor with a measurement target, i.e. the wrist artery. As far as the biosignal measurement is concerned, in view of what has been set forth above the important point is that particularly the site of the casing where the sensor is located is pressed against the artery such that when the wrist is moved, the contact of the sensor with the skin remains as good as possible, thereby enabling as high measuring accuracy as possible.

In order to achieve the above-mentioned object, the arrangement of the invention for measuring a biosignal is characterized by what is disclosed in the characterizing part of claim 1.

The idea underlying the invention is thus that the measuring arrangement comprises an element which operates like a spring and produces a force which, with respect to the fastener, turns the casing towards the measurement target, i.e. the wrist artery underneath the surface of the skin, pressing the measuring sensor tighter against the surface of the skin. The element is thus used for improving the contact of the measuring sensor with the surface of the skin such that instead of pressing the wrist over the entire area covered by the fastener, it is exactly the measuring sensor which is pressed against the skin and the artery by the pressing force caused by the element. An advantage achieved by the arrangement of the invention is thus improved adaptation to the measurement target on a person's wrist and, consequently, improved contact with the surface of the skin and the wrist artery when the position of the wrist varies and when the wrist is moved. The preferred embodiments and further implementations of the invention shown in closer detail herein emphasize and acknowledge the advantages of the invention.

According to the invention, the casing comprising the measuring sensor is pressed against the skin by an element, preferably a spring element, such as a helical spring or alternatively a leaf spring. As far as the implementation of the arrangement is concerned, it is then preferable that the element is supported at a fastening part, such as a fastening pin, of a fastener, such as a fastening strip. According to a preferred embodiment, the spring element is a pre-bent, shaped part made of plastic, arranged to be an integrated part of the fastener.

The measuring sensor of the measuring arrangement is preferably located on the undersurface of the casing which is pressed against the measurement target, i.e. the surface of the skin and substantially in the vicinity of the upper edge of the casing. The advantage achieved is that a hinge-like joint turning with respect to one fulcrum is then provided between the casing and the fastener, the fastening part serving as the fulcrum of the joint, and the spring element enables a force directed towards the measurement target to be concentrated on the upper edge of the casing.

Since the arrangement of the invention is preferably designated to measure a pressure pulse signal from the wrist, the fastener is preferably a wristband. In the arrangement of the invention, the biosignal is a pressure signal, in which case the measuring sensor is a pressure sensor. The arrangement is well suited to use in connection with a biosignal measuring device, such as a heart rate monitor, or alternatively, in connection with a blood pressure apparatus.

BRIEF DESCRIPTION OF THE DRAWINGS

The invention is now described in closer detail in connection with the preferred embodiments of the invention and with reference to the accompanying drawings, in which.

DETAILED DESCRIPTION OF THE REFERRED EMBODIMENTS

Figure 1:
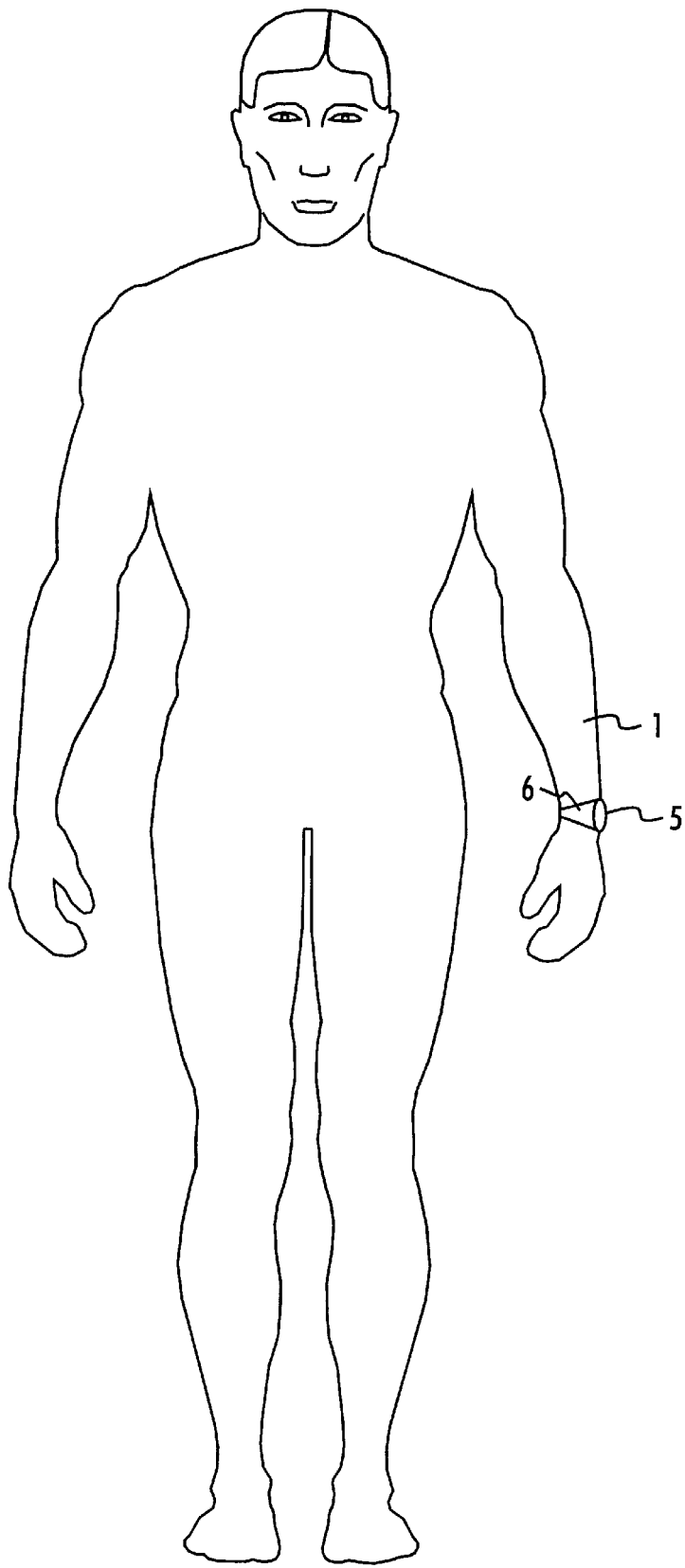
FIG. 1 shows a human body wherefrom a biosignal is measured from the surface of the skin of the body, a biosignal measuring arrangement being attached to the wrist of the body.
Figure 2:
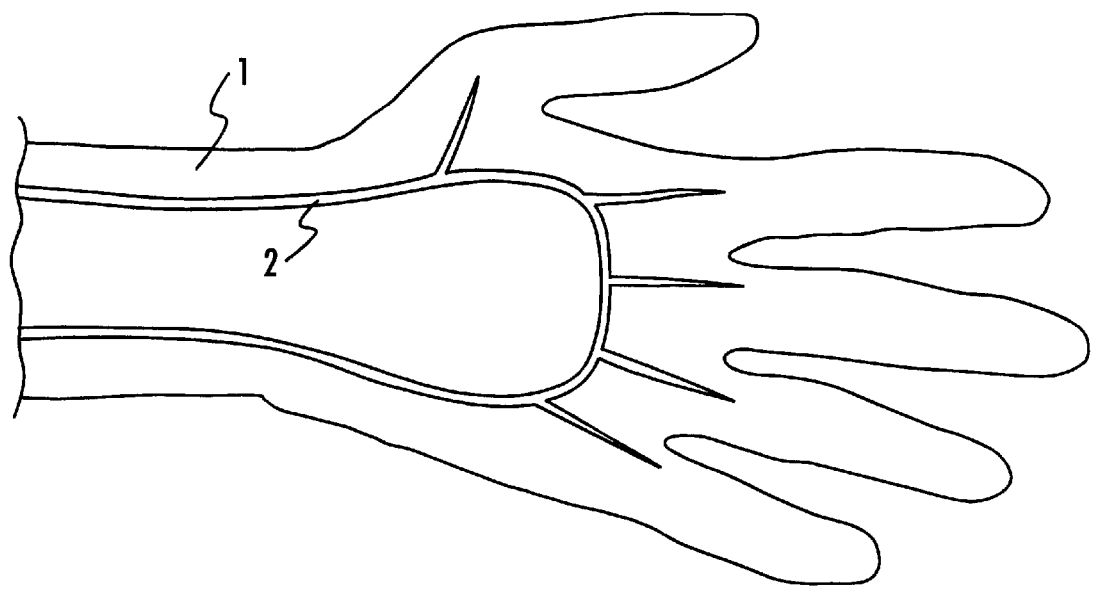
FIG. 2 shows a hand belonging to the body, showing how the wrist artery is located.
Figure 3:
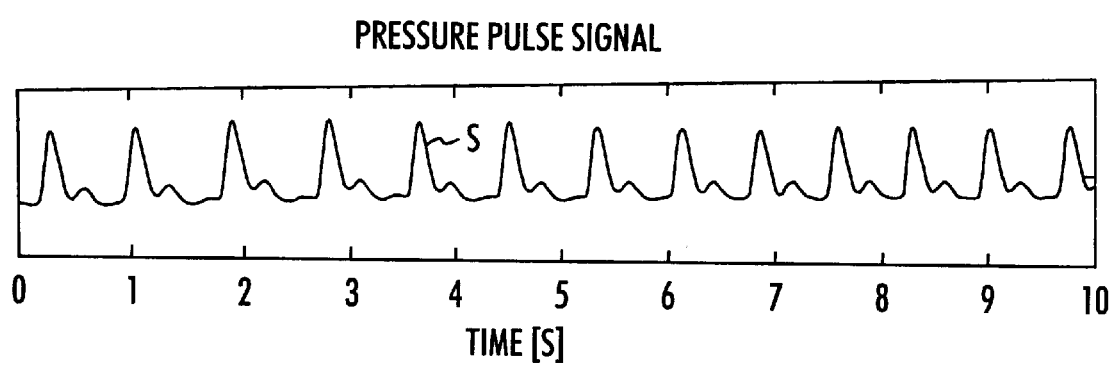
FIG. 3 shows a pressure pulse signal to be measured by a biosignal measuring arrangement of the invention.

In the following, the invention will be described on the basis of the accompanying drawings. FIG. 1 shows a living human body wherefrom a biosignal is measured from the surface of the skin 1 of the body. In FIG. 1, a biosignal measuring device according to a preferred embodiment of the invention, such as a heart rate monitor, is arranged on the wrist of the person, the device being connected to a fastener 6, such as a casing 5 attached to the wristband 6. In FIG. 2, the living body is represented by a hand belonging to the body, the hand showing how an artery 2, such as a wrist artery 2, is located. Preferably, the signal to be measured is a pressure pulse signal S to be measured from the wrist artery 2, in which case a measuring sensor 300 of the measuring arrangement is a pressure sensor 300. The pressure pulse signal is shown in FIG. 3.

Figure 4:
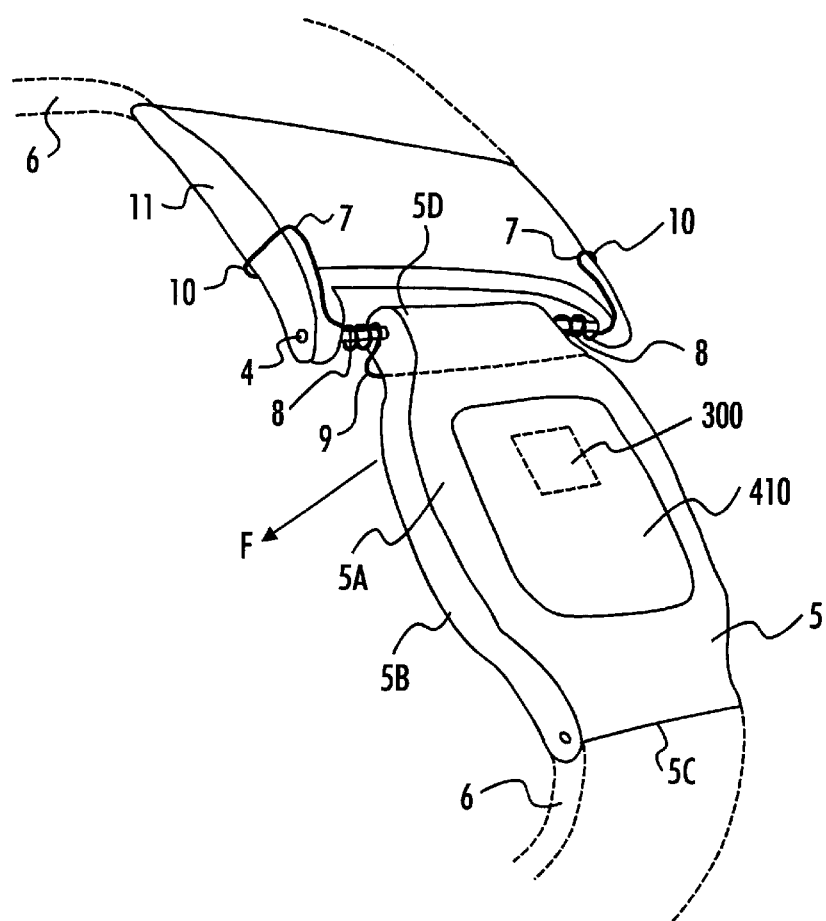
FIG. 4 shows the biosignal measuring arrangement of the invention to be attached to the wrist, the arrangement comprising a helical-spring-type element of the invention.
Figure 5:
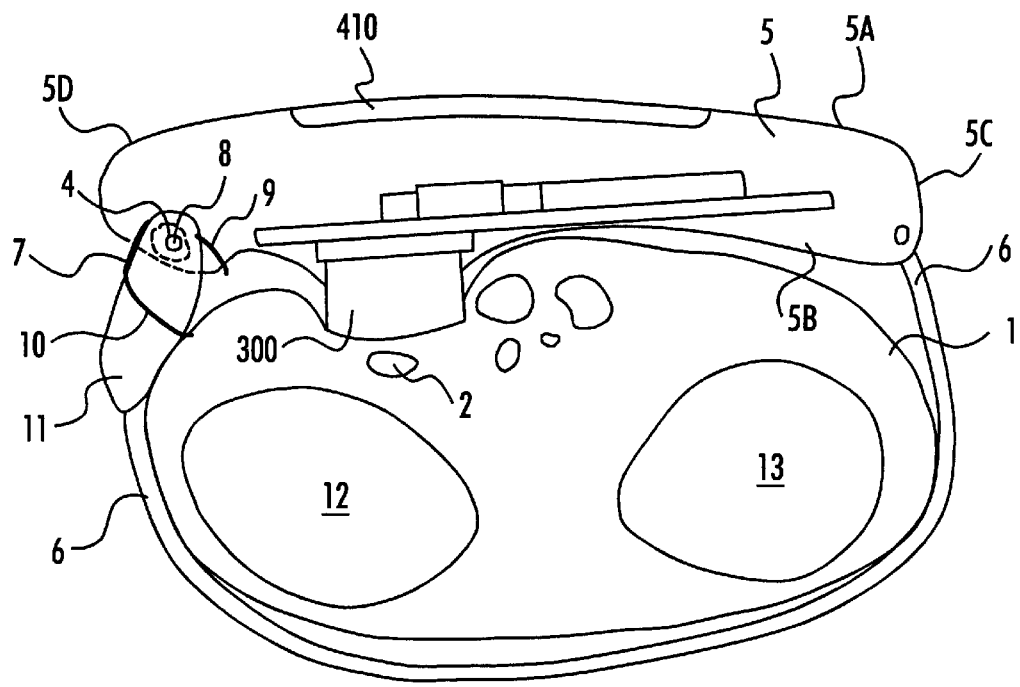
FIG. 5 shows the biosignal measuring arrangement of the invention arranged in a wristband as seen from the direction of a cross-section of the wrist.

FIGS. 4 and 5 show a measuring arrangement of the heart rate monitor type of the preferred embodiment of the invention wherein all components of the device are arranged in one casing 5. In FIG. 5, reference numbers 12 and 13 designate the radius and the ulna respectively. In the measuring arrangement, the pressure pulse signal S measured from the wrist artery 2 is measured by the pressure sensor 300. As can be seen from FIG. 5, the sensor 300 is situated at the wrist artery 2 such that the sensor 300 is located on top of the wrist artery while the sensor 300 is pressed tightly against the surface 1 of the skin in order to obtain as good contact with the artery as possible. The contact of the sensor 300 with the surface 1 of the skin may either be direct, in which case the sensor 300 directly touches the surface 1 of the skin, or alternatively, the contact may be indirect, in which case e.g. a plastic strip operating as a pressure transmission element is arranged between the sensor 300 and the surface 1 of the skin. In addition, the surface of the sensor 300 may be provided with a protecting film made of plastic or rubber to block dust and damp.

The components of the measuring arrangement, such as the pressure sensor 300, measurement data display 410 and/or measurement data memory 411, are arranged in the casing 5. The measuring arrangement is kept in place on the wrist on the surface 1 of the person's skin by the fastener 6, which is preferably a straplike wristband 6. The fastener 6 is attached to the casing 5 by a fastening part 8, which is preferably a pin 8. The joint thus comprises the pin 8 arranged between the fastener 6 and the casing 5 as well as clamps arranged at the ends of the fastener 6 and the casing 5 and provided with a hole 4 in their transverse direction, the fastening part 8 being arranged through the holes 4. The joint also serves as a hinge. The fastener 6 is appropriately tightened around the wrist and locked by a clasp 11. The fastener 6 may also be a collar comprising two collar halves attached to the casing 5, at least one of the halves being hinged with respect to the casing in order to enable the collar to be set in place.

The casing 5 comprises an upside 5A and an underside 5B. The measuring sensor 300 of the arrangement is then preferably arranged on the underside 5B of the casing 5 which in a normal operating situation is pressed against the measurement target. Furthermore, the measuring sensor 300 is arranged substantially in the vicinity of an upper edge 5D of the casing 5, according to the location of the wrist artery.

The object of the invention is thus to improve the contact of the sensor 300 with the wrist artery 2. The idea of the invention is thus that the arrangement comprises an element 7, which is a spring element comprising lever-like supporting surfaces located at a first end 9 and a second end 10 of the element, and a spring part located therebetween. The first end 9 of the element 7 rests on the casing 5 while the second end 10 of the element rests on the fastener 6. The element 7 is preferably arranged in the joint between the fastener 6 and the upper edge 5D of the casing 5 such that the element 7 produces a force F which, with respect to the fastener 6, turns the casing 5 substantially towards the measurement target, i.e. the surface 1 of the skin and the artery 2 underneath, thus pressing the upper edge 5D of the casing 5 against the measurement target 1.

The above-described arrangement is used for directing a pressing force against the surface 1 of the skin and the artery 2 instead of pressing the wrist over the entire area covered by the fastener 6. As can be seen from FIGS. 4, 5, 6, 7A and 7B, the element 7 is arranged between the casing 5 and the fastener 6 of the measuring arrangement.

Figure 6:
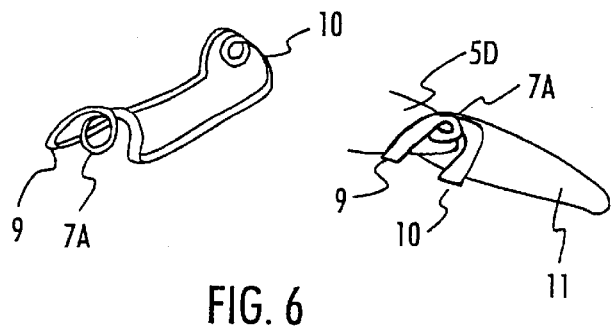
FIG. 6 shows the helical-spring-type element of the biosignal measuring arrangement of the invention.

In the preferred embodiment of FIGS. 4, 5 and 6, the element 7 rests on a joint pin 8 of a pin joint between the casing 5 and the fastener 6. The force needed to improve the artery contact is thus such that the part of the casing 5 where the sensor 300 is located is to be pressed tightly against the surface 1 of the skin. Thus, in order to obtain a correctly directed force, the first end 9 of the element 7 rests on the casing 5 while the second end 10 rests on the clasp 11 of the fastener 6. The force stored in the spring element of the element 7 is thus transmitted to the edge 5D of the casing 5 which is located at the first end 9 of the element 7 and which comprises the sensor 300 when in its middle part the element 7 rests on the joint pin 8 of the pin joint and when the element 7 uses the clasp 11 of the fastener 6 as its second fulcrum at the second end 10 of the element 7.

In the case of the collar fastener, the element 7 is situated in connection with the hinged half of the collar, this half being the one which is situated on the side of the casing 5 where the sensor 300 is arranged. The element 7 otherwise operates in a similar manner to that in the case of the strap arrangement in order to achieve as good contact with the artery as possible.

The element 7 is a spring element. As illustrated by FIGS. 4, 5 and 6, the spring element is preferably a helical spring 7A provided with supporting surfaces at its ends 9, 10 to enable the element to rest on the casing 5 and the fastener 6, such as on the clasp 11 of the fastener 6 in the solution of FIGS. 4, 5 and 6. The middle part of the spring element comprises a helix to store the spring force producing the necessary force F directed towards the artery 2. In an embodiment of the invention, in order to enable the spring element to operate effectively, the helix in the middle part of the spring element is punctured by the joint pin 8 of the pin joint between the casing 5 and the fastener 6, whereby the spring element rests on its place at the joint pin 8, which thus operates as a third fulcrum of the spring element. Thus supported, the spring element transmits the pressing power to the end of the casing 5 where the sensor 300 is arranged, resting on the fastener 6 and the joint pin 8 of the pin joint.

The element 7 may also be a leaf-spring-type 7B spring element. The ends of the leaf spring 7B are also provided with spring element supporting surfaces by means of which the element rests on the casing 5 and the fastener 6. In an embodiment of the invention in order to enable the spring element to operate effectively, the middle point of the spring element is shaped such that it can be punctured by the joint pin 8 of the pin joint between the casing 5 and the fastener 6, whereby the spring element rests on its place at the joint pin 8, which thus operates a third fulcrum of the spring element. Thus supported, the spring element transmits the pressing force to the upper edge 5D of the casing 5 where the sensor 300 is arranged and presses the sensor 300 against the measurement target 1, resting on the fastener 6 and the joint pin 8 of the pin joint.

Figure 7A:
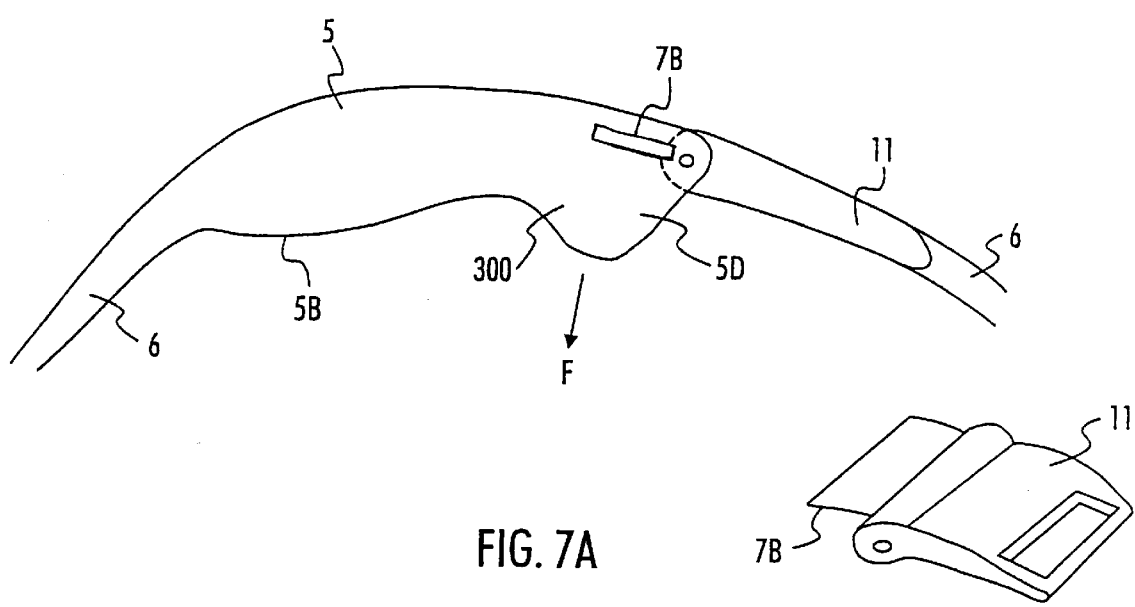
FIG. 7a shows the biosignal measuring arrangement of the invention to be attached to the wrist which comprises the helical-spring-type element of the invention arranged in a clasp of a fastener.

Implemented by the leaf-spring-type spring element according to FIG. 7A, the structure of the element 7B may-also be such that the supporting surface of the spring element of the leaf spring 7B located at the end of the fastener 6 rests on the fastener 6, e.g. on the clasp 11 of the fastener 6. The supporting surface of the leaf spring 7B at the end of the casing 5 is arranged to rest on the casing 5. The leaf spring 7B then preferably comprises a structural part which is pre-bent or shaped such that when set in its proper place it transmits to the casing 5 a force which is with respect to the fastener 6 directed substantially towards the measurement target, i.e. the surface 1 of the skin and the artery 2 underneath, thus pressing the upper edge 5D of the casing 5 against the measurement target 1. The leaf spring 7B may be made of plastic or metal.

Figure 7B:
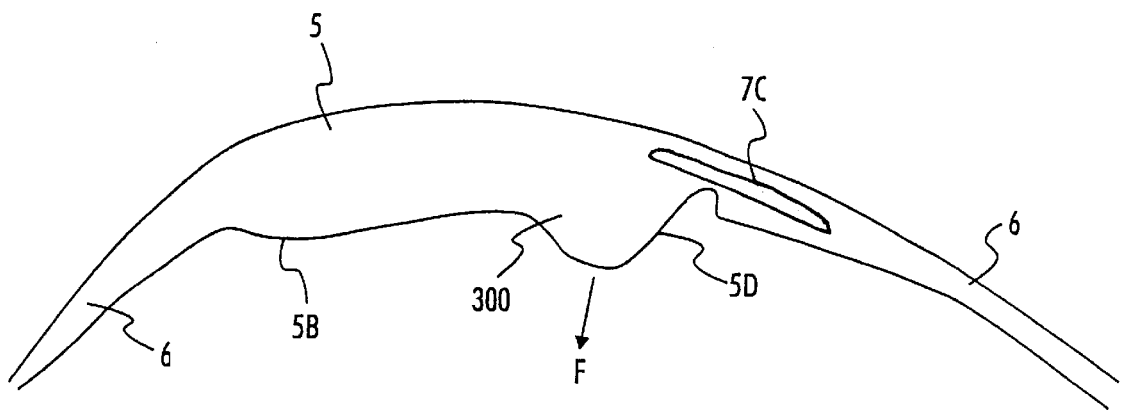
FIG. 7b shows the biosignal measuring arrangement of the invention to be attached to the wrist which comprises the helical-spring-type element of the invention arranged to be part of the wristband.

FIG. 7B shows a measuring arrangement of the invention wherein the casing 5 and the fastener 6 constitute an integral whole. During the manufacture of the casing-fastener entity, the joint between the casing 5 and the fastener 6 at the end 5D of the casing 5 comprising the measuring sensor 300 is provided with a leaf-spring-type spring element 7C. The leaf spring 7C is then a pre-bent plastic structure shaped such that the spring mechanism 7C is directly integrated in the structure of the casing-fastener entity. Thus implemented, the supporting surface of the element 7C located at the end of the fastener 6 rests on the fastener 6 while the supporting surface of the element 7C located at the end of the casing 5 is rests on the casing 5. When the measuring arrangement is tightened in its appropriate place, i.e. around the wrist, the element 7C at the joint between the casing 5 and the fastener 6 bends, the element 7C resisting this bending; consequently, the element 7C transmits to the casing 5 a force which is with respect to the fastener 6 directed substantially towards the measurement target, i.e. the surface 1 of the skin and the artery 2 underneath, thus pressing the upper edge 5D of the casing 5 against the measurement target 1.

Since the arrangement of the invention is preferably intended for measuring the pressure pulse signal S from the pulse of the wrist artery 2, the fastener 6 is preferably a wristband to be attached to the wrist. The wristband may then resemble a strap, collar or the like. As far as the implementation of the arrangement is concerned, it is then preferable that the element 7 is supported at the fastening pin 8 of the fastener 6.

The casing 5 of the measuring arrangement of the preferred embodiment of the invention is attached around the wrist by the fastener 6 such that the casing 5 and the sensor 300 resting thereon are placed on the underside of the wrist, i.e. on the side where the wrist artery 2 is located in the human wrist.

If all components of the measuring arrangement are arranged in the same casing 5, as in the embodiment of FIGS. 5 and 6, the casing 5 is then preferably placed on the underside of the wrist as far as using the measuring device is concerned. The casing 5 is tightened around the wrist by means of the fastener 6.

It is also conceivable that not all components of the measuring arrangement are arranged in a single casing but the sensor 300 is arranged in a casing to be placed on the underside of the wrist whereas a casing comprising a display device is placed on the upper surface of the wrist. The casings are tightened around the wrist by using the same fastener 6. The element 7 is then situated between the casing 5 comprising the sensor 300 and the fastener 6 such that the element 7 rests on the joint pin 8 of the pin joint between the casing and the fastener 6 in a similar manner to that in connection with the embodiment comprising only one casing. Data transmission between the casing comprising the sensor 300 and the other casing comprising the display device can be implemented by using wired data transmission utilizing wires arranged between the casings. Another alternative is to use wireless data transmission between the casings based e.g. on using inductive data transmission or a radio signal by employing e.g. technology called Bluetooth.

As to the application areas of the invention, the invention can be applied primarily to small personal heart rate monitors to be worn on the wrist. The measuring arrangement in FIGS. 4 and 5 is a measuring arrangement used in a heart rate monitor to be attached to a person's wrist or somewhere else in the body. The wristband in FIGS. 4 and 5 is designated by reference number 6.

In the application, the pressure sensor 300 measures the pressure pulse of the artery 2 from the surface 1 of the skin of the human body, and a heart rate value is calculated on the basis of this pulse. The measuring arrangement is then a measuring arrangement for measuring the pressure pulse of the artery 2 from the surface 1 of the skin of the human body. In accordance with FIG. 8, the measuring arrangement then comprises a determining means 400 for determining the heart beat value on the basis of the measurement of the pressure pulse of the artery 2. Prior to the means 400 for determining the heart rate value there may be provided signal modifying elements known per se or otherwise, such as a filter 401, an amplifier 402 and an A/D converter 403.

Figure 8:
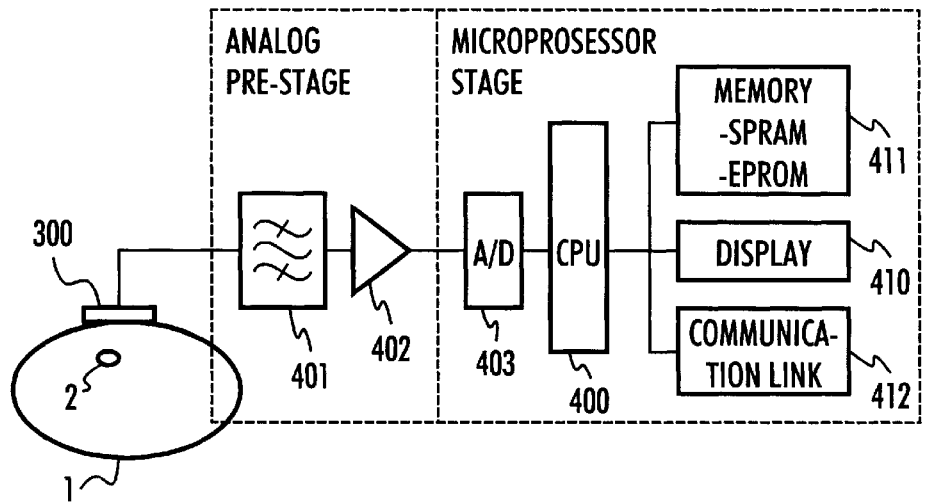
FIG. 8 is a diagram schematically showing the biosignal measuring arrangement of the invention applied to heart rate measurement.

The filter 401 in FIG. 8 is a band-pass filter. The pass band of the band-pass filter is preferably located within an area of 1 to 10 Hz.

In FIG. 8, the filter 401 and the amplifier 402 implement an analogue pre-stage. In FIGS. 4, 5 and 8 the measuring arrangement further comprises the display 410 in connection with the determining means 400 for displaying the heart rate value. In an embodiment, the determining means 400 counts the number of received pressure pulses per time unit and indicates the heart rate value on the display 410. In a second embodiment, the determining means 400 measures the time intervals of successive pressure pulses, calculates the heart rate on the basis of the received information and indicates the heart rate on the display 410. In addition, a memory 411 and a transmission connection 412, such as an RS-232 connection or a Bluetooth connection, communicate with the determining means 400, the transmission connection enabling heart rate information to be transmitted to a reader and further e.g. to a personal computer. Naturally, the connection 412 may be used for data transmission in the reverse direction as well.

Figure 9:
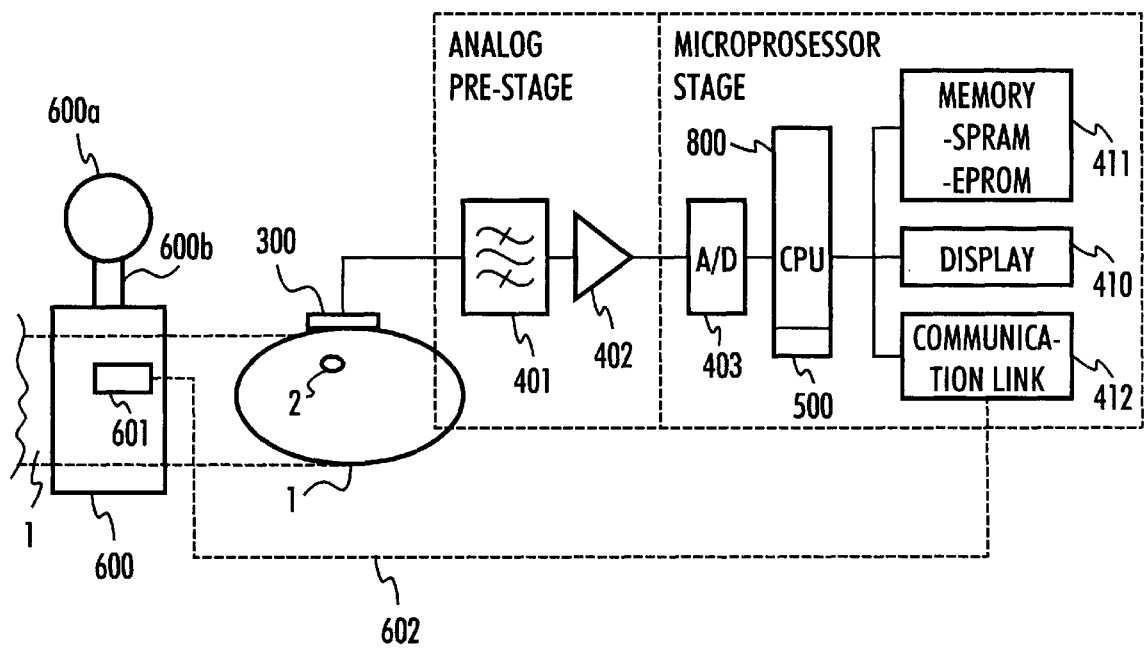
FIG. 9 is a diagram schematically showing the biosignal measuring arrangement of the invention applied to blood pressure measurement.

FIG. 9 shows a preferred embodiment for blood pressure measurement. The measuring arrangement is then a measuring arrangement for measuring the pressure pulse of the artery 2 from the surface 1 of the skin of a human body. The measuring arrangement further comprises a pulse strength determining means 500 for finding out the strength of the pressure pulse of the artery 2. In addition, a sensor 601 is connected to the measuring arrangement to measure the strength of the effective pressure generated by a pressure generator 600, which sensor 601 has a wired or wireless connection 602 to the measuring arrangement and which in this application can be considered to be part of the measuring arrangement. The effective pressure refers to the pressure which squeezes a blood vessel. When the effective pressure is sufficiently high, the pressure pulse stops, i.e. the pressure sensor 300 detects no pressure pulse, in which case no measurement signal will be forwarded to block 500. When the strength of the effective pressure is lowered again, i.e. when the pressure of the pressure generator 600 is lowered, blood starts flowing again and the pressure sensor 300 produces a signal to block 500, which thus determines the strength of the pressure pulse. The pressure generator 600 is e.g. a pressure cuff 600 which comprises a pressure pump 600a and a pressure line 600b used for conveying the pressure from the pressure pump 600a to the cuff 600.

In the embodiment of FIG. 9, the measuring arrangement also comprises the filter 401, amplifier 402, A/D converter 403, display 410, memory 411 and possibly a data transmission connection 412, such as an RS connection 412. As to the implementation of these blocks, reference is made to the implementation of the corresponding blocks in FIG. 8.

The value of the effective pressure produced by the pressure generator 600, or the information on the basis of which the effective pressure value can be calculated, is transferred from the sensor 601 to the measuring arrangement e.g. through the RS-232 connection 412 or through another wireless or wired data transmission connection. The transmission connection is designated by reference number 602. The transmission connection 602 may be based e.g. on an inductive coupling between blocks 601 and 412.

The measuring arrangement in FIG. 9 further comprises a blood pressure determining means 800 communicating with the pressure pulse strength determining means 500. The information obtained from the sensor 601 e.g. through the connection 412, 602 on the strength of the effective pressure is also routed to the blood pressure determining means 800. Controlled by the pressure pulse strength determining means 500, the blood pressure determining means 800 determines a blood pressure value on the basis of the signal of the sensor 601 measuring the strength of the effective pressure, the blood pressure value being displayed on the display 410 of the measuring arrangement. When the signal of the pressure pulse strength determining means 500 starts decreasing, the blood pressure determining means 800 determines, i.e. finds out, that a diastolic pressure PDIAS value is the same as the value of the effective pressure at the particular moment obtained from the sensor 601. Similarly, when the amplitude of the signal of the pressure pulse strength determining means 500 becomes sufficiently low or is no longer able to be detected or approaches a particular limit value close to zero, the blood pressure value determining means 800 determines that a systolic pressure PSYS value is the same as the value of the effective pressure at the particular moment obtained from the sensor 601.

Figure 10:
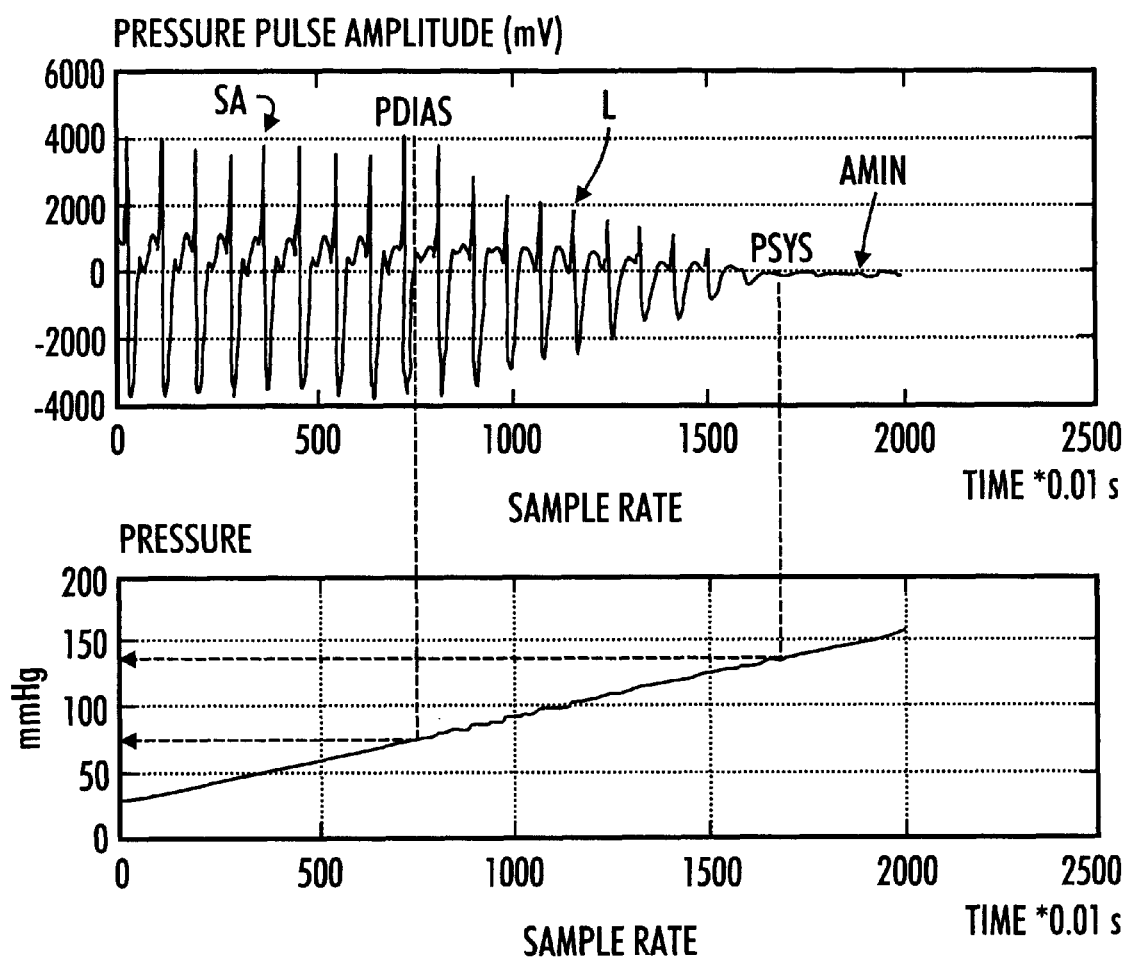
FIG. 10 shows a pressure pulse signal of a blood pressure measurement application and an effective pressing force.

Referring to FIGS. 9 and 10, it is noted that said varying effective pressure is an ascending effective pressure. The blood pressure is thus measured when the effective pressure is being raised by the pressure generator 600. The measurement is more convenient to the person being measured during the ascending pressure since the effective pressure does not have to be raised too high. This means that in the measurement carried out during the ascending effective pressure, the diastolic pressure PDIAS is determined on the basis of a strength of the effective pressure which prevails when in the pressure pulse measurement, e.g. during the measurement of the pressure pulse amplitude in blocks 500 and 800, it is detected that the strength of the pressure pulse, i.e. the amplitude, starts decreasing. Similarly, the systolic pressure PSYS is determined on the basis of a strength of the effective pressure which prevails when in the measurement of the pressure pulse, e.g. during the measurement of the pressure pulse amplitude in blocks 500 and 800, it is detected that the pressure pulse amplitude stops decreasing.

To be more exact, still referring to FIG. 10, the method is most preferably such that in the measurement carried out during the ascending effective pressure, the diastolic pressure PDIAS is determined on the basis of the effective pressure of the same strength which prevails when during the measurement of the pressure pulse, e.g. in the measurement of the pressure pulse amplitude, it is detected that the substantially constant value of the pressure pulse, such as an amplitude with a constant value, starts decreasing substantially directly linearly. Similarly, the systolic pressure PSYS is determined on the basis of the strength of the effective pressure which prevails when in the measurement of the pressure pulse amplitude it is detected that the amplitude of the substantially directly linearly descending pressure pulse stops decreasing and reaches its minimum value AMIN substantially corresponding to zero. The pulse strength determining means 500 enables such points to be detected more easily and, additionally, more accurate measurements to be achieved.

The heart rate value determining means 400, pulse strength determining means 500 and blood pressure value determining means 800 may be implemented by a programmable processor, an ASIC (Application Specific Integrated Circuit) circuit, a separate component or by employing mixed technology, which refers to a combination of two or more abovementioned techniques. The alternative embodiments disclosed above also apply to the filter 401 and the amplifier 402 which, according to the Applicant's view, can be implemented extremely well by the ASIC technology, although e.g. operational amplifiers, resistors and capacitors may alternatively be used as well. The display 410 is e.g. a matrix display.

In FIG. 9, blocks 401, 402 and 410 to 412 may be implemented in a similar manner to that shown for blocks 401, 402 and 410 to 412 in FIG. 8. Blocks 500 and 800 differ most from block 400 since block 500, compared to block 400, must also be able to find out the strength of the pressure pulse signal at any given moment in place of or in addition to mere calculation of the number of pulses (or calculation of the length of time intervals between the pulses). Block 800 must also to be able to interpret what the change in the output information supplied by block 500 means. The operation of block 800 is thus controlled by rules which, in accordance with FIG. 10, indicate what each change in the output information supplied by block 500 means. As to FIGS. 8 and 9, it is stated that the sensor 300 is connected to the filter 401 wherein the signal is filtered. The filter 401, in turn, is connected to an intermediate amplifier 402 which amplifies the filtered signal. The intermediate repeater 402, in turn, is connected to an A/D converter 403 which converts an analogue signal into a digital one. The A/D converter, in turn, is connected to the processor 400/500/800.

Although the invention has been described above with reference to one exemplary embodiment only, it is obvious that the invention is not restricted thereto but it can be modified in many ways within the scope of the inventive idea disclosed in the attached claims.

What is claimed is:

1. An arrangement for measuring a biosignal from a living body, comprising:
   a casing (5),
   a measuring sensor (300) which rests on the casing (5) and which is to be arranged against a measurement target (1) on the body, and
   a fastener (6) for fastening the casing (5) to the measurement target (1),
   characterized in that
      the arrangement comprises an element (7) whose first end (9) rests on the casing (5) and whose second end (10) rests on the fastener (6) such that the element (7) is arranged to produce a force which turns the casing (5) substantially towards the measurement target (1) with respect to the fastener (6).

2. An arrangement as claimed in claim 1, characterized in that the casing (5) comprises an upside (5A) and an underside (5B), whereby the measuring sensor (300) of the arrangement is arranged on the underside (5B) of the casing (5) pressing against the measurement target.

3. An arrangement as claimed in claim 2, characterized in that the measuring sensor (300) is arranged substantially in the vicinity of an upper edge (5D) of the casing (5).

4. An arrangement as claimed in claim 2, characterized in that the element (7) is arranged at a joint between the fastener (6) and the upper edge (5D) of the casing (5) to press the upper edge (5D) of the casing (5) against the measurement target (1).

5. An arrangement as claimed in claim 2, characterized in that the element (7) is a spring element.

6. An arrangement as claimed in claim 3, characterized in that the element (7) is arranged at a joint between the fastener (6) and the upper edge (5D) of the casing (5) to press the upper edge (5D) of the casing (5) against the measurement target (1).

7. An arrangement as claimed in claim 3, characterized in that the element (7) is a spring element.

8. An arrangement as claimed in claim 1, characterized in that the element (7) is arranged at a joint between the fastener (6) and the upper edge (5D) of the casing (5) to press the upper edge (5D) of the casing (5) against the measurement target (1).

9. An arrangement as claimed in claim 8, characterized in that the arrangement comprises a fastening part (8) connecting the casing (5) and the fastener (6) and in that the element (7) is arranged substantially at the fastening part (8) connecting the casing (5) and the fastener (6).

10. An arrangement as claimed in claim 8, characterized in that the element (7) is a spring element.

11. An arrangement as claimed in claim 9, characterized in that the fastening part (8) is a pin.

12. An arrangement as claimed in claim 11, characterized in that the element (7) is a spring element.

13. An arrangement as claimed in claim 9, characterized in that the element (7) is a spring element.

14. An arrangement as claimed in claim 1, characterized in that the element (7) is a spring element.

15. An arrangement as claimed in claim 14, characterized in that between the ends (9, 10) the element (7) rests on the fastening part (8) connecting the casing (5) and the fastener (6).

16. An arrangement as claimed in claim 15, characterized in that the spring element is a helical spring (7A).

17. An arrangement as claimed in claim 15, characterized in that the spring element is a leaf spring (7B).

18. An arrangement as claimed in claim 14, characterized in that the spring element is a helical spring (7A).

19. An arrangement as claimed in claim 14, characterized in that the spring element is a leaf spring (7B).

20. An arrangement as claimed in claim 19, characterized in that the leaf spring (7B) comprises a pre-bent and/or shaped structural part.

21. An arrangement as claimed in claim 20, characterized in that the biosignal measurement target (1) is a human artery (2), whereby the measuring arrangement is arranged to measure a pressure pulse of the artery (2).

22. An arrangement as claimed in claim 21, characterized in that the biosignal measuring arrangement is to be attached to a human body.

23. An arrangement as claimed in claim 21, characterized in that the biosignal measuring arrangement is to be attached to a human wrist.

24. An arrangement as claimed in claim 20, characterized in that the biosignal measuring arrangement is to be attached to a human body.

25. An arrangement as claimed in claim 20, characterized in that the leaf spring (7B) is part of the fastener (6).

26. An arrangement as claimed in claim 20, characterized in that the biosignal measuring arrangement is to be attached to a human wrist.

27. An arrangement as claimed in claim 19, characterized in that the leaf spring (7B) is part of the fastener (6).

28. An arrangement as claimed in claim 27, characterized in that the leaf spring (7B) is made of plastic.

29. An arrangement as claimed in claim 28, characterized in that the biosignal measuring arrangement is a measuring arrangement for measuring a human heart rate.

30. An arrangement as claimed in claim 29, characterized in that the fastener (6) is a wristband.

31. An arrangement as claimed in claim 28, characterized in that the biosignal measuring arrangement is to be attached to a human body.

32. An arrangement as claimed in claim 28, characterized in that the biosignal measuring arrangement is to be attached to a human wrist.

33. An arrangement as claimed in claim 27, characterized in that the measuring sensor (300) is a pressure sensor.

34. An arrangement as claimed in claim 33, characterized in the biosignal measuring arrangement is to be attached onto a human wrist.

35. An arrangement as claimed in claim 27, characterized in that the biosignal measuring arrangement is to be attached to a human body.

36. An arrangement as claimed in claim 27, characterized in that the biosignal measuring arrangement is to be attached to a human wrist.

37. An arrangement for measuring a biosignal from a measurement target on a living body, comprising:
   a casing (5),
   a measuring sensor (300) for producing a measurement signal, which sensor (300) rests on the casing (5) and is to be arranged against a measurement target (1) on the body
   a calculating unit (400, 401, 402, 403) for producing measurement information, which calculating unit (400, 401, 402, 403) is arranged in the casing (5) to process the measurement signal
   a measurement information display (410) or memory (411) communicating with the calculating unit (400, 401, 402, 403) for displaying and/or storing the measurement information, and a fastener (6) for fastening the casing (5) to the measurement target (1), characterized in that the arrangement comprises an element (7) whose first end (9) rests on the casing (5) and whose second end (10) rests on the fastener (6) such that the element (7) is arranged to produce a force which turns the casing (5) substantially towards the measurement target (1) with respect to the fastener (6).

38. An arrangement as claimed in claim 37, characterized in that the biosignal measuring arrangement is a measuring arrangement for measuring human blood pressure, wherein a pressure pulse signal to be measured is utilized in determining blood pressure.

39. An arrangement as claimed in claim 37, characterized in that the biosignal measuring arrangement is to be attached to a human body.

40. An arrangement as claimed in claim 37, characterized in that the biosignal measuring arrangement is to be attached to a human wrist.

* * * * *